United States Patent
Onuma et al.

(10) Patent No.: US 9,526,517 B2
(45) Date of Patent: Dec. 27, 2016

(54) PROBE, TREATMENT DEVICE, AND TREATMENT SYSTEM

(71) Applicant: OLYMPUS CORPORATION, Hachioji-shi, Tokyo (JP)

(72) Inventors: Chie Onuma, Fuchu (JP); Manabu Ishikawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/003,422

(22) Filed: Jan. 21, 2016

(65) Prior Publication Data

US 2016/0143648 A1    May 26, 2016

Related U.S. Application Data

(63) Continuation of application No. PCT/JP2014/075460, filed on Sep. 25, 2014.
(Continued)

(51) Int. Cl.
*A61B 17/32* (2006.01)
*A61B 17/16* (2006.01)
(Continued)

(52) U.S. Cl.
CPC ....... *A61B 17/320068* (2013.01); *A61B 17/16* (2013.01); *A61B 17/1604* (2013.01);
(Continued)

(58) Field of Classification Search
CPC ............... A61B 17/16; A61B 17/1604; A61B 17/22004; A61B 2017/22011; A61B 17/32; A61B 17/320068; A61B 2017/320072; A61C 1/07
See application file for complete search history.

(56) References Cited

U.S. PATENT DOCUMENTS

2007/0038157 A1    2/2007 Yamada et al.
2008/0194999 A1    8/2008 Yamaha et al.
(Continued)

FOREIGN PATENT DOCUMENTS

FR    3018184 A1 *  9/2015 ............ A61B 17/14
JP    H07-255736 A    10/1995
(Continued)

OTHER PUBLICATIONS

Machine Translation of FR3018184 Retrieved from <http://translationportal.epo.org/emtp/translate?ACTION=description-retrieval&COUNTRY=FR&ENGINE=google&FORMAT=docdb&KIND=A1&LOCALE=en_EP&NUMBER=3018184&OPS=ops.epo.org%2F3.1&SRCLANG=fr&TRGLANG=en&apikey=TSMqTfrVAvNtryGl8Qlfbozj8DnAGlqJ&PDF=YbvWtoX1eU3HEipUASVfvxbXqBW-_h1hORjmMfnGo6crE> on Jul. 27, 2016.*
(Continued)

*Primary Examiner* — Larry E Waggle, Jr.
(74) *Attorney, Agent, or Firm* — Oliff PLC

(57) ABSTRACT

A probe which is configured to treat a bone by ultrasonic vibration, includes: a treatment section which is arranged on a distal end side of a vibration transmitting section, to which the ultrasonic vibration is transmitted through the vibration transmitting section. The treatment section includes: a cutting blade that includes a treatment surface, and cuts and treats the bone by the treatment surface; a protrusion that is provided at a position different from the cutting blade, protrudes in a direction different from the protruding direction of the treatment surface of the cutting blade, marks the bone, and defines a position of the bone to be treated with the cutting blade; and a regulation surface that is formed at a position where the protrusion is provided, and regulates
(Continued)

entrance of the protrusion into the bone beyond a predetermined level.

6 Claims, 14 Drawing Sheets

Related U.S. Application Data

(60) Provisional application No. 61/883,520, filed on Sep. 27, 2013.

(51) Int. Cl.
    *A61C 1/07*     (2006.01)
    *A61B 17/3211*     (2006.01)
    *A61N 7/00*     (2006.01)
    *A61B 17/00*     (2006.01)
    *A61B 17/22*     (2006.01)

(52) U.S. Cl.
    CPC ...... *A61B 17/1628* (2013.01); *A61B 17/3211* (2013.01); *A61B 90/361* (2016.02); *A61B 90/37* (2016.02); *A61C 1/07* (2013.01); *A61N 7/00* (2013.01); *A61B 2017/00398* (2013.01); *A61B 2017/22011* (2013.01); *A61B 2017/320072* (2013.01)

(56) References Cited

U.S. PATENT DOCUMENTS

| | | |
|---|---|---|
| 2009/0247823 A1 | 10/2009 | Yamamoto |
| 2010/0106173 A1 | 4/2010 | Yoshimine |
| 2012/0215243 A1 | 8/2012 | Fujii et al. |
| 2015/0142033 A1* | 5/2015 | Stulen ............ A61B 17/320068 606/169 |

FOREIGN PATENT DOCUMENTS

| | | |
|---|---|---|
| JP | H10-225460 A | 8/1998 |
| JP | 2004-237100 A | 8/2004 |
| JP | 2008-194457 A | 8/2008 |
| JP | 2012-170627 A | 9/2012 |
| WO | 2006/048966 A1 | 5/2006 |
| WO | 2007/034708 A1 | 3/2007 |
| WO | 2010/047395 A1 | 4/2010 |
| WO | 2012/079025 A1 | 6/2012 |

OTHER PUBLICATIONS

Mar. 4, 2014 Search Report issued in International Patent Application No. PCT/JP2014/051945.
Dec. 22, 2014 Search Report issued in International Patent Application No. PCT/JP2014/075460.
Apr. 7, 2016 International Preliminary Report on Patentability issued in International Application No. PCT/JP2014/075460.

* cited by examiner

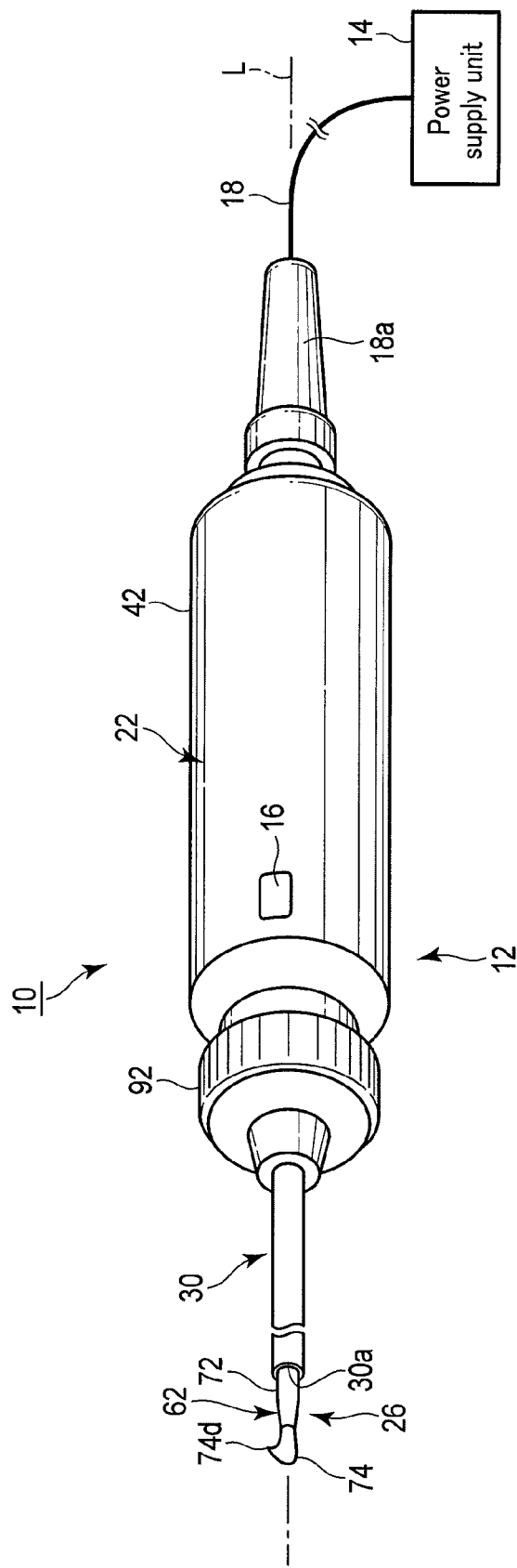
F I G. 1

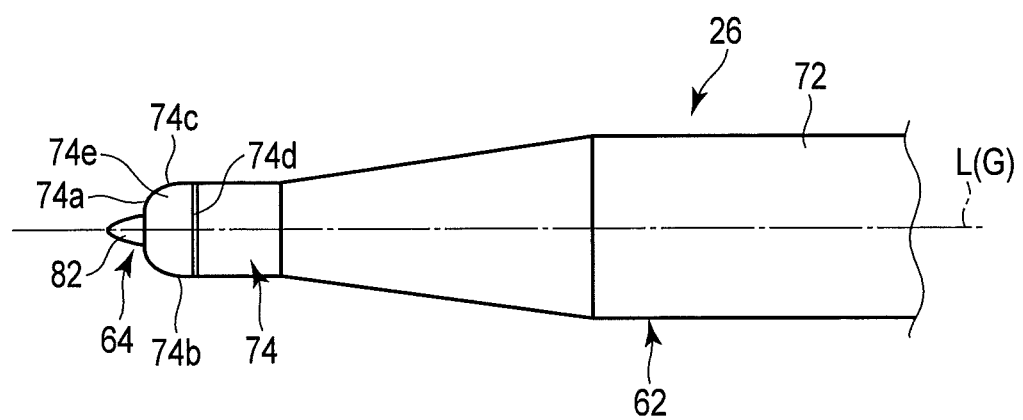
F I G. 6C

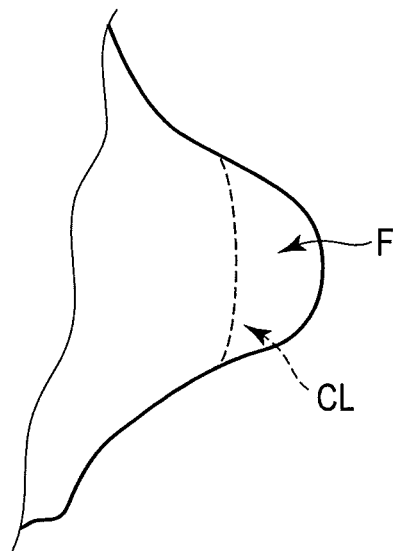
F I G. 7A
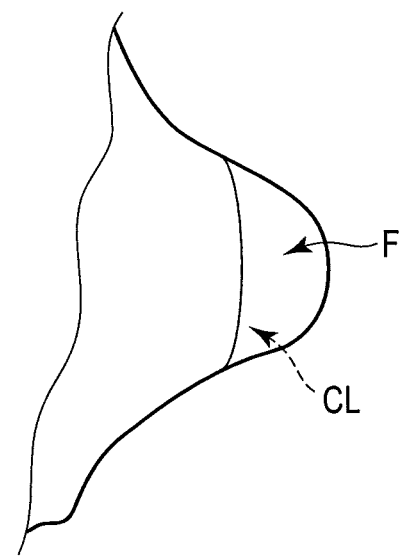
F I G. 7B

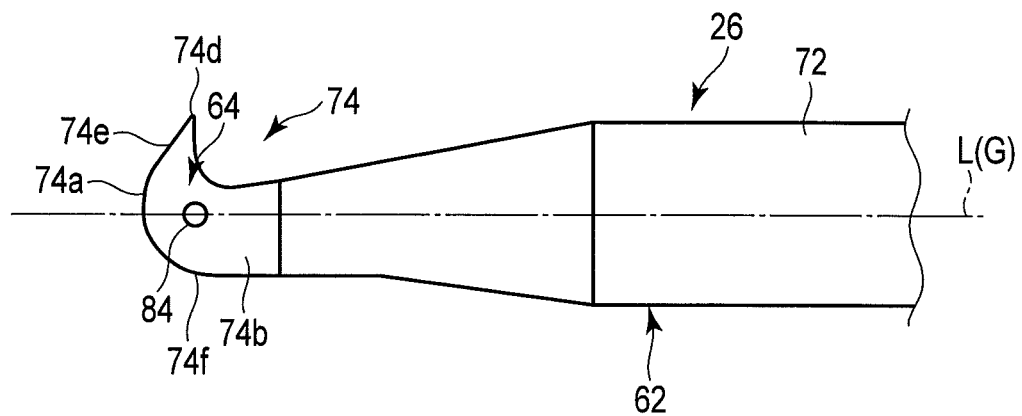
F I G. 9A
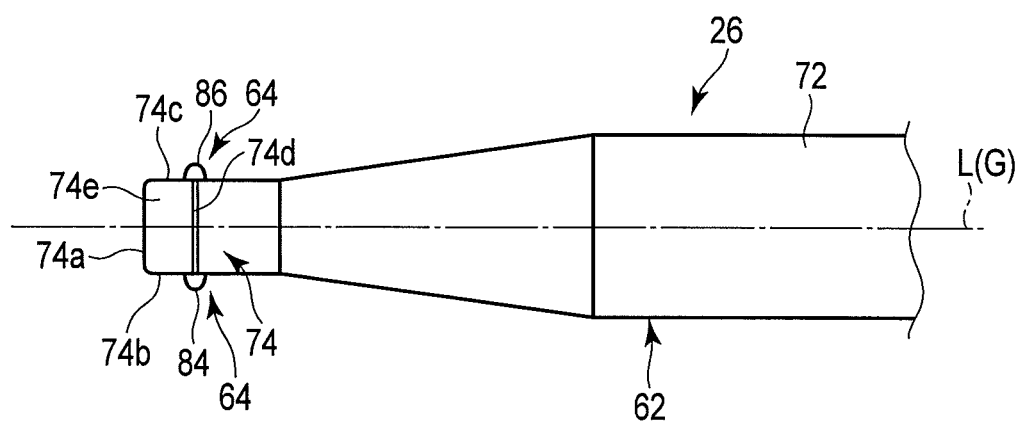
F I G. 9B

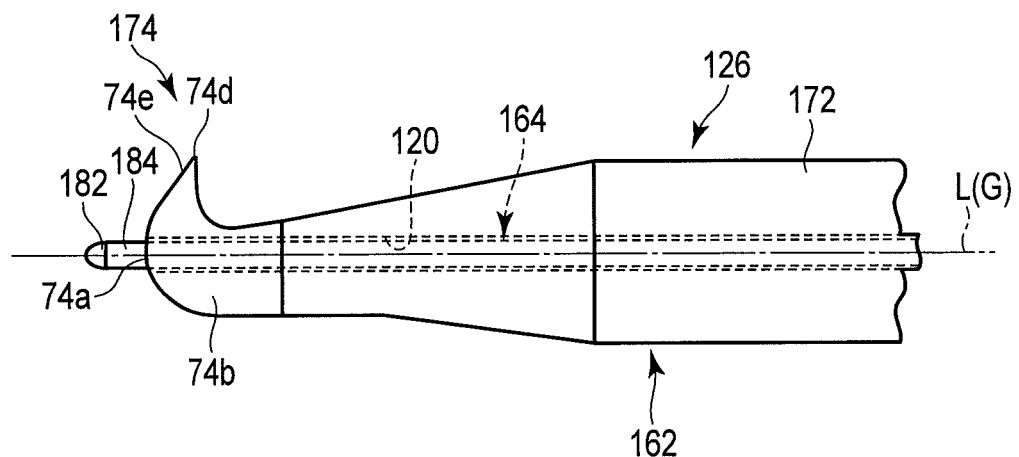
F I G. 13A
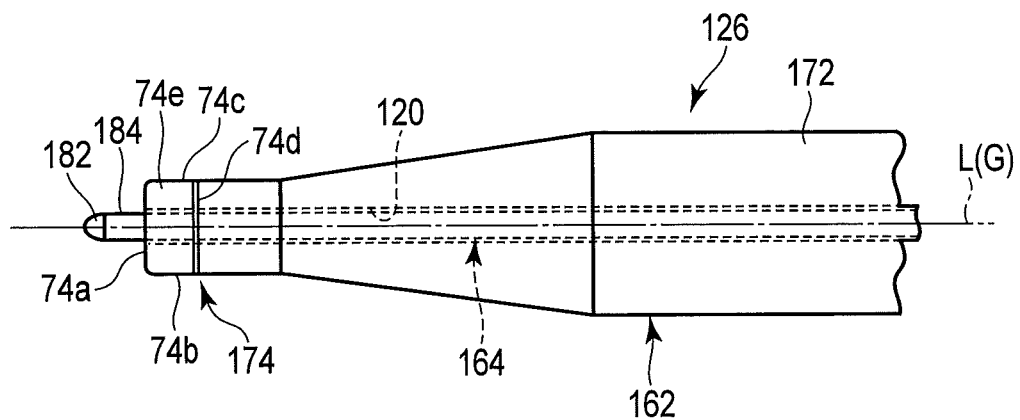
F I G. 13B

PROBE, TREATMENT DEVICE, AND TREATMENT SYSTEM

CROSS-REFERENCE TO RELATED APPLICATIONS

This application is a Continuation Application of PCT Application No. PCT/JP2014/075460, filed Sep. 25, 2014 and based upon and claiming the benefit of priority from prior PCT Application No. PCT/JP2014/051945, filed Jan. 29, 2014 and the benefit of U.S. Provisional Application No. 61/883,520, filed Sep. 27, 2013, the entire contents of all of which are incorporated herein by reference.

BACKGROUND OF THE INVENTION

1. Field of the Invention

The present invention relates to a probe, a treatment device, and a treatment system that is configured to treat a biological tissue with the use of ultrasonic vibration.

2. Description of the Related Art

In case of giving a treatment of, e.g., cutting a part of a bone through a narrow cavity by using a treatment device having a probe disclosed in, e.g., Jpn. Pat. Appln. KOKAI Publication No. Hei 7-255736, marking a treatment target region in advance is preferable. Further, in the marking, it is possible to use such a treatment device as disclosed in, e.g., Jpn. Pat. Appln. KOKAI Publication No. 2004-237100 as a different device.

In a flow of the treatment in this case, the treatment device for marking accesses a region as a treatment target through an introduction pipeline (a port) to perform the marking while observing the region as the treatment target with an endoscope or the like. Then, the treatment device for marking is removed from the introduction pipeline, a treatment device configured to treat the treatment target is put into the introduction pipeline to access the region as the treatment target, and the treatment is given in accordance with a marked position.

BRIEF SUMMARY OF THE INVENTION

According to one aspect of the present invention, a probe which is configured to treat a bone by ultrasonic vibration, includes: a vibration transmitting section that defines a longitudinal axis along which the ultrasonic vibration is transmitted from a proximal end side toward a distal end side; and a treatment section which is arranged on the distal end side of the vibration transmitting section, to which the ultrasonic vibration is transmitted through the vibration transmitting section, and the treatment section including: a cutting blade that includes a treatment surface which protrudes in a direction crossing the longitudinal axis, and cuts and treats the bone by the treatment surface; a protrusion that is provided at a position different from the cutting blade, protrudes in a direction different from the protruding direction of the treatment surface of the cutting blade, marks the bone, and defines a position of the bone to be treated with the cutting blade; and a regulation surface that is formed at a position where the protrusion is provided, and regulates entrance of the protrusion into the bone beyond a predetermined level.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing a treatment system according to a first embodiment;

FIG. 6C is a schematic top view showing the hook-shaped treatment section and the knife-shaped marking section with a recognizable width in the probe unit of the treatment device of the treatment system according to the first modification of the first embodiment;

FIG. 7A is a schematic view showing a state that a grip section is moved in the same direction as a width direction of a marker and the biological tissue is linearly marked to define a treatment target region of the biological tissue by the treatment system according to the first modification of the first embodiment;

FIG. 7B is a schematic view showing a state that marking is performed in a dotted pattern to define the treatment target region of the biological tissue with the use of the treatment system according to the first modification of the first embodiment;

FIG. 9A is a schematic side elevation showing a hook-shaped treatment section and a marking section in a probe unit of a treatment device of a treatment system according to a third modification of the first embodiment;

FIG. 9B is a schematic top view showing a hook-shaped treatment section and a marking section in a probe unit of a treatment device of a treatment system according to a further modification of the third modification of the first embodiment;

FIG. 13A is a schematic side elevation showing a hook-shaped treatment section and a marking section protruding from a distal end of the treatment section in a probe unit of a treatment device of the treatment system according to the second embodiment; and FIG. 13B is a schematic top view showing the hook-shaped treatment section and the marking section protruding from the distal end of the treatment section in the probe unit of the treatment device of the treatment system according to the second embodiment.

DETAILED DESCRIPTION OF THE INVENTION

Figure 2:
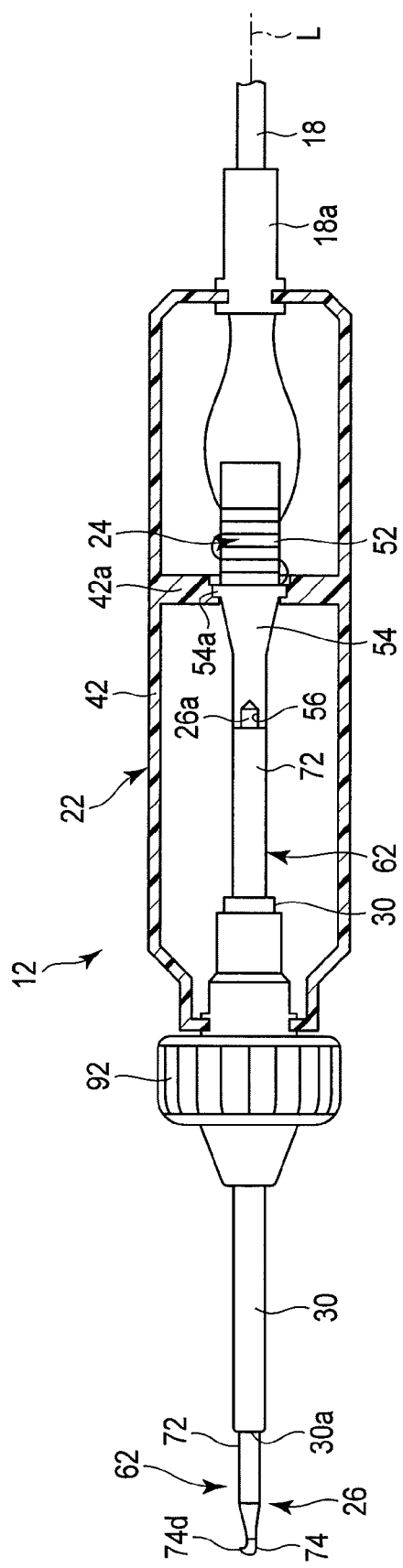
FIG. 2 is a schematic partial longitudinal sectional view showing a treatment device of a treatment system according to the first embodiment.

A mode for carrying out the present invention will now be described hereinafter with reference to the drawings.

A first embodiment will now be described with reference to FIG. 1 to FIG. 5.

As shown in FIG. 1, a treatment system 10 according to this embodiment includes a treatment device 12 used to give a treatment to a biological tissue (e.g., a bone or a cartilage), a power supply unit (a controller) 14, and a switch section 16 such as a foot switch or a hand switch. The treatment device 12 is connected with the power supply unit 14 through a cable 18. The cable 18 supplies or receives a signal between the switch section 16 and the power supply unit 14, or supplies electric power controlled by the power supply unit 14 to a later-described ultrasonic transducer 52 of the treatment device 12. It is to be noted that, in this embodiment, the cable 18 is extended from a cable protector 18a at a proximal end of the treatment device 12, and a non-illustrated connector at a distal end of the cable 18 is attachable to or detachable from the power supply unit 14.

In this embodiment, a description will be given on the assumption that a hand switch arranged on a grip section 22 of the treatment device 12 is used as the switch section 16, but use of anon-illustrated foot switch connected to the power supply unit 14 is also preferable.

As shown in FIG. 2, the treatment device 12 includes a grip section 22 gripped by a user, an ultrasonic transducer unit 24, and a probe unit 26. In other words, the treatment device 12 has the probe unit 26, the ultrasonic transducer unit 24 that transmits ultrasonic vibration to the probe unit 26, and the grip section 22 that supports the ultrasonic transducer unit 24 and is gripped by the user.

The grip section 22 has a central axis on a longitudinal axis L defined by the probe unit 26. The transducer unit 24, the probe unit 26, and a tubular body (a sheath) 30 are arranged to the grip section 22 with the longitudinal axis L at the center.

The grip section 22 includes a cylindrical exterior case 42 that preferably has electrical insulating properties. The ultrasonic transducer unit 24 is supported inside the exterior case 42.

The transducer unit 24 includes an ultrasonic transducer 52 that generates the ultrasonic vibration by appropriate supply of electric power from the power supply unit 14 shown in FIG. 1 and a conical horn 54 that enlarges the amplitude of the ultrasonic vibration generated by the ultrasonic transducer 52. That is, the transducer unit 24 generates the ultrasonic vibration in response to supply of the electric power.

As the ultrasonic transducer 52, for example, a BLT type including piezoelectric elements is used. The horn 54 is disposed at a male screw 26a at a proximal end of the probe unit 26 through a connection screw (a female screw) 56. The horn 54 includes an outer flange 54a radially and outwardly protruding from the longitudinal axis L of the horn 54. The outer flange 54a is placed at a node position of the vibration when the ultrasonic vibration is transmitted from the ultrasonic transducer 52.

An inner flange 42a radially and inwardly protruding from an inner peripheral surface is formed on the exterior case 42. When the outer flange 54a of the horn 54 engages with the inner flange 42a of the exterior case 42, the transducer unit 24 and the probe unit 26 are supported by the exterior case 42. That is, the exterior case 42 is arranged between the grip section 22 and the ultrasonic transducer unit 24, and supports the ultrasonic transducer unit 24 at the node position of the ultrasonic vibration.

It is to be noted that, in this embodiment, a description will be given as to an example where the ultrasonic transducer unit 24 is supported in the exterior case 42, but forming the ultrasonic transducer unit 24 to be attachable to/detachable from the exterior case 42 is also preferable.

The probe unit 26 shown in FIG. 1 to FIG. 3 is designed in such a manner that its entire length becomes approximately an integral multiple of a half wavelength of the ultrasonic vibration. The probe unit 26 has a rod-shaped probe 62 made of a metal such as a titanium alloy and a protruding marking section 64 provided on the probe 62.

The probe 62 has a rod-shaped probe main body (a vibration transmitting section) 72 and a treatment section 74 provided on a distal end side of the probe main body 72. The ultrasonic vibration generated by the ultrasonic transducer 52 is subjected to amplitude enlargement by the horn 54, transmitted to the distal end side from a proximal end side of the probe main body 72, and transmitted to the treatment section 74 through the probe main body 72. The treatment section 74 can treat a treatment target region by the ultrasonic vibration transmitted through the probe main body (the vibration transmitting section) 72. Thus, the probe 62 can transmit the ultrasonic vibration from the ultrasonic transducer unit 24 and treat a biological tissue by an effect of the ultrasonic vibration transmitted to the treatment section 74 at the distal end portion thereof.

Here, the tubular body 30 is formed of a cylindrical body. The tubular body 30 is provided on the distal end side of the grip section 22, and covers an outer periphery of the probe main body 72 of the probe unit 26 in a state that the treatment section 74 at the distal end portion of the probe unit 26 is arranged and exposed on the distal end side to a distal end 30a of the tubular body 30. A core of the tubular body 30 is preferably made of a material having rigidity such as a stainless alloy, and an outer surface and an inner surface of the core are preferably covered with a material having electrical insulating properties, e.g., PTFE, respectively. A spacer is preferably arranged between the inner peripheral surface of the tubular body 30 and a node position of the vibration of the probe main body 72.

The treatment section 74 according to this embodiment is formed into a hook shape. The treatment section 74 includes a distal end (a distal end face) 74a, a pair of side surfaces (surface portions) 74b and 74c, and an edge face region (a treatment surface) 74d formed on a proximal end side of the distal end face (a surface portion) 74a. In this embodiment, the distal end face 74a is formed as a flat surface portion. The longitudinal axis L crosses the distal end face 74a, and the side surfaces 74b and 74c are provided at positions deviating from the longitudinal axis L. In particular, the distal end face 74a is preferably subjected to low-friction coating that lowers a friction force more on a biological tissue than on other regions. The edge face region 74d is provided at or near an antinodeposition of the ultrasonic vibration, and can cut an abutting biological tissue when the ultrasonic vibration is transmitted in a state that this region abuts on the biological tissue. It is to be noted that a continuous surface denoted by reference sign 74e between the distal end face 74a and the edge face region 74d is appropriately formed as a flat surface or a curved surface. Further, a continuous surface 74f that is provided on the opposite side of the edge face region (the treatment surface) 74d, orthogonal to the side surface 74b and 74c, and continuous with the distal end face 74a is formed of a curved surface. It is to be noted that each of a boundary between the distal end face 74a and the continuous surface 74e and a boundary between the distal end face 74a and the continuous surface 74f is formed as an obtuse angle that is larger than 90° and smaller than 180°, namely, close to 180°. Therefore, the distal end face 74a is smoothly continuous with the continuous surface 74e, and the distal end face 74a is smoothly continuous with the continuous surface 74f, respectively. In other words, no edge is formed between the distal end face 74a and the continuous face 74e and between the distal end face 74a and the continuous surface 74f. It is to be noted that a position of each of the continuous surfaces 74e and 74f close to the distal end face 74a is preferably subjected to the low-friction coating to be continuous with the coating of the distal end face 74a.

Figure 3A:
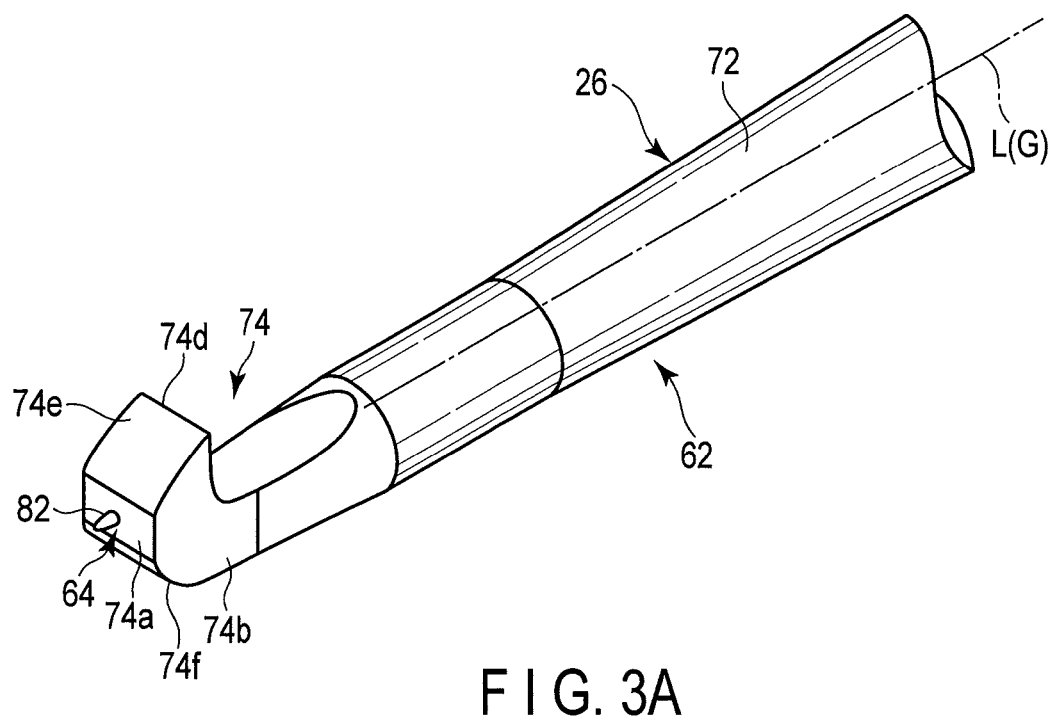
FIG. 3A is a schematic perspective view showing a hook-shaped treatment section and a marking section in a probe unit of the treatment device of the treatment system according to the first embodiment.
Figure 3B:
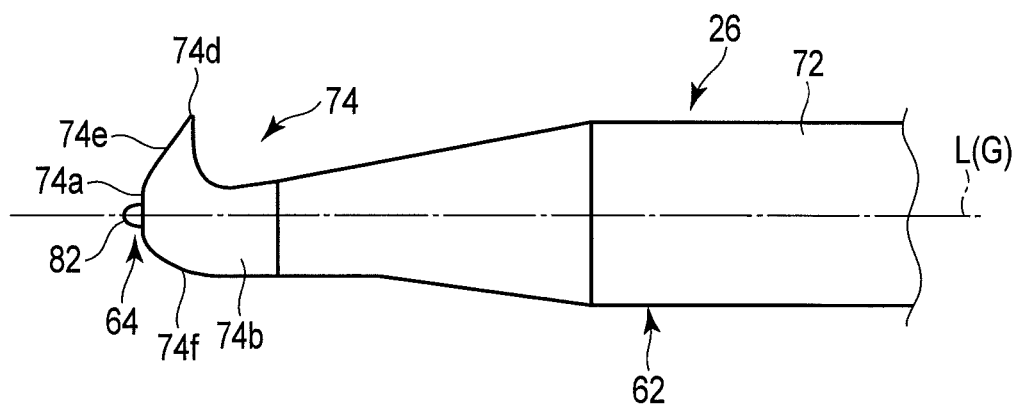
FIG. 3B is a schematic side elevation showing the hook-shaped treatment section and the marking section in the probe unit of the treatment device of the treatment system according to the first embodiment.
Figure 3C:
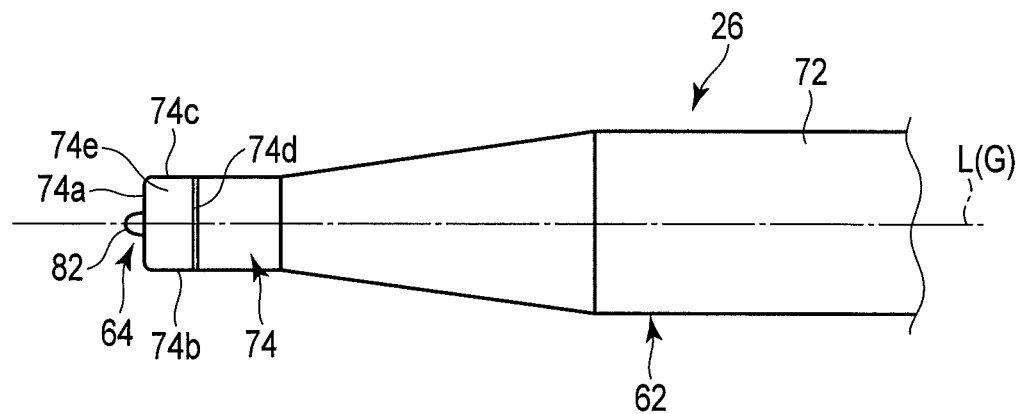
FIG. 3C is a schematic top view showing the hook-shaped treatment section and the marking section in the probe unit of the treatment device of the treatment system according to the first embodiment.

A marking section 64 shown in FIG. 3A to FIG. 3C is preferably integrated with the treatment section 74 of the probe 62. In this embodiment, the marking section 64 has a marker (a protrusion) 82, which protrudes on the treatment section 74 toward the distal end side along the longitudinal axis L, on the distal end face 74a of the treatment section 74. The longitudinal axis L is defined in the marking section 64 by the probe main body 72 and the treatment section 74, and the marking section 64 is arranged on the distal end side of the treatment section 74 along the longitudinal axis L. Therefore, the marking section 64 is arranged in a region different from a treatment region in the treatment section 74. The marking section 64 can perform marking on a biological tissue to define a treatment target region to be treated by the treatment section 74 using the ultrasonic vibration transmitted to the treatment section 74. A size (a surface area) of a distal end (a function region of the ultrasonic vibration) of the marker 82 of the marking section 64 in particular is formed to be sufficiently smaller than a surface area of the distal end face 74a of the treatment section 74 of the probe 62. The marker 82 is formed as a protrusion protruding from the distal end face 74a of the treatment section 74. The marker 82 is preferably formed into a tapered shape tapered toward the distal end, a semispherical shape, or a substantially elliptic conical shape as long as it can form a hole in a biological tissue such as a bone or a cartilage to perform marking. Thus, the marker 82 is preferably symmetrically formed in a periaxial direction of the longitudinal axis L. It is to be noted that an area of the marker 82 that comes into contact with a biological tissue is sufficiently smaller than an area of the edge face region 74d that comes into contact with the biological tissue. That is, an area of the marker 82 that can cut the biological tissue at a time is smaller than an area of the edge face region 74d that can cut the biological tissue at a time.

The marker 82 is preferably formed on a virtual center of gravity line connecting a center of gravity position on the proximal end side with a counterpart on the distal end position in a lateral cross section of the probe 62 orthogonal to the longitudinal axis L. That is, the marking section 64 is arranged at a center of gravity position G on the distal end face 74a of the treatment section 74. Furthermore, the edge face region 74d is placed on the proximal end side of the marker 82 along the longitudinal axis L. Thus, when the ultrasonic vibration is transmitted from the proximal end side toward the distal end side of the probe 62, a vibration balance of the probe 62 is maintained without causing abnormal vibration, and the edge face region 74d of the treatment section 74 can appropriately treat the biological tissue.

A rotary operation knob 92 shown in FIG. 1 and FIG. 2 is disposed to the exterior case 42 to be rotatable in the periaxial direction of the longitudinal axis L of the tubular body 30. The rotary operation knob 92 supports the vibration node position of the probe main body 72 of the probe 62 to rotate together. Thus, when the rotary operation knob 92 turns to the exterior case 42, the tubular body 30 and the probe unit 26 as well as the ultrasonic transducer unit 24 fixed on the proximal end side of the probe unit 26 turn together.

It is to be noted that, in this embodiment, the rotary operation knob 92 is arranged, but it is not necessarily required, and appropriately providing the rotary operation knob 92 can suffice.

The power supply unit 14 according to this embodiment is electrically connected to the ultrasonic transducer 52. Moreover, when the switch section 16 electrically connected to the power supply unit 14 is appropriately operated, electric power can be supplied to the ultrasonic transducer 52 from the power supply unit 14, and the ultrasonic vibration can be appropriately generated from the ultrasonic transducer 52.

A function of the treatment system 10 according to this embodiment will now be described.

For example, in case of scraping a surface F (see FIG. 4A to FIG. 5) of a biological tissue such as a bone, scraping is performed while observing the biological tissue of a part to be scraped with, e.g., an arthroscope (not shown) which is a type of endoscope. Here, for simplicity, a description will be given on the assumption that the treatment section 74 of the probe unit 26 can be kept being observed with the arthroscope without moving the arthroscope.

A user decides a region where a treatment is given to the biological tissue (a treatment target region) based on, e.g., an observation result of the arthroscope.

The user observes a direction of the probe unit 26 to the surface F of the biological tissue by using the non-illustrated endoscope, e.g., the arthroscope while gripping the grip section 22. The rotary operation knob 92 is operated as required, and the marker 82 of the marking section 64 is rotated in the periaxial direction of the longitudinal axis L to enable observation using the arthroscope.

Figure 4A:
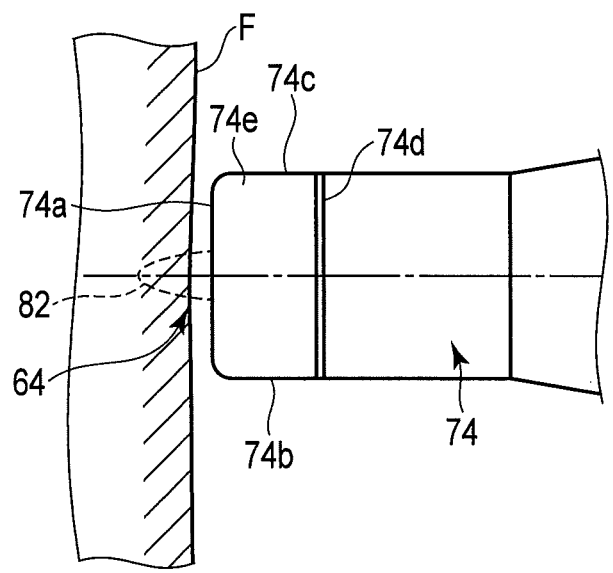
FIG. 4A is a schematic view showing a state that a distal end face of the treatment section is apart from a surface of a biological tissue when a hole is formed in the surface of the biological tissue by ultrasonic vibration with the use of the marking section provided on the distal end face of the hook-shaped treatment section in the probe unit of the treatment device of the treatment system according to the first embodiment.
Figure 4B:
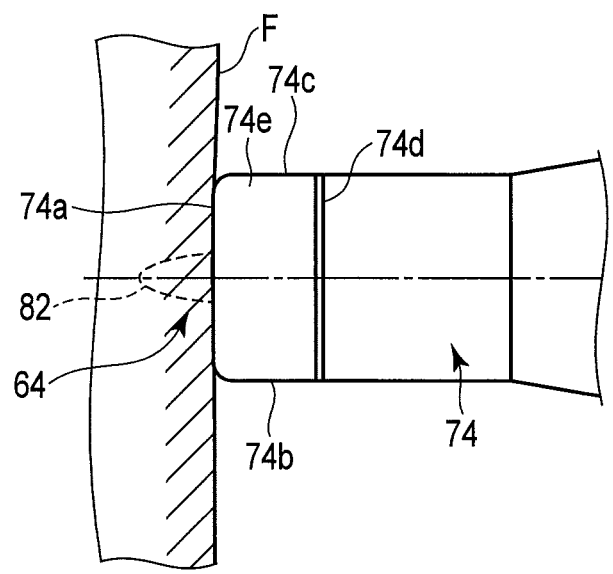
FIG. 4B is a schematic view showing a state that the distal end face of the treatment section abuts on the surface of the biological tissue when a hole is formed in the surface of the biological tissue by the ultrasonic vibration with the use of the marking section provided on the distal end face of the hook-shaped treatment section in the probe unit of the treatment device of the treatment system according to the first embodiment.
Figure 5:
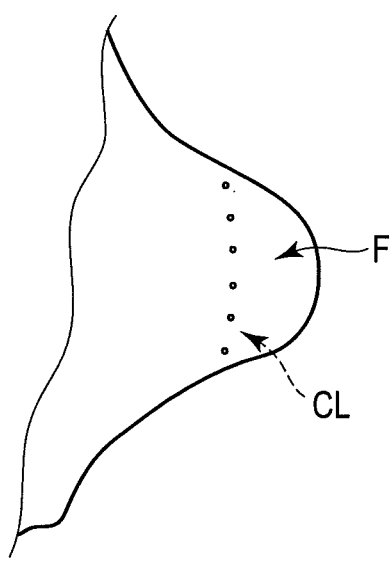
FIG. 5 is a schematic view showing a state that marking is performed in a dotted pattern by the marking section shown in FIG. 3A to FIG. 4B to define a treatment target region of the biological tissue with the use of the treatment system according to the first embodiment.

The switch section 16, e.g., a hand switch is pressed, the ultrasonic transducer 52 is driven by the electric power from the power supply unit 14, and the ultrasonic vibration is transmitted to the probe unit 26. Here, longitudinal vibration from the ultrasonic transducer 52 is transmitted to the marker 82 of the marking section 64 through the horn 54, the probe main body 72, and the treatment section 74. A small hole is formed in the biological tissue or the biological tissue is slightly scraped with the use of the distal end of the marker 82 by the function of the ultrasonic vibration transmitted to the marker 82. At this time, the ultrasonic vibration is transmitted or not transmitted to the probe unit 26 by appropriately operating the switch section 16. When a hole is formed or slight scraping is performed in this manner, it is preferable to operate the grip section 22 without bringing the distal end face 74a of the treatment section 71 into contact with the surface F of the biological tissue as shown in FIG. 4A. When the distal end face 74a of the treatment section 74 is brought into contact with the surface F of the biological tissue as shown in FIG. 4B, the distal end face 74a functions as a regulation surface that regulates entrance of the marker 82 into the biological tissue. That is, the distal end face 74a of the treatment section 74 functions as a stopper that defines an amount of entrance of the marker 82 (the marking section 64) into the biological tissue. In other words, the distal end face 74a is formed of a flat surface or a curved surface having no portion that is caught on the biological tissue to prevent a treatment (cutting) from being given to the contacted biological tissue even if it comes into contact with the biological tissue. The amount of entrance of the marker 82 into the surface F of the biological tissue is defined by a length of the marker 82 along the longitudinal axis L. The distal end face 74a of the treatment section 74 is formed to have a larger surface area than the distal end (the function region of the ultrasonic vibration) of the marker 82 (the marking section 64). Thus, when the ultrasonic vibration has been transmitted to the treatment section 74, the biological tissue abutting on the distal end face 74a can be prevented from being affected by the ultrasonic vibration, and the biological tissue can be protected.

It is to be noted that, in this embodiment, the distal end face 74a is subjected to the low-friction coating, and hence an influence of transmission of the ultrasonic vibration on the biological tissue that can abut on the distal end face 74a due to the ultrasonic vibration can be reduced to be smaller than an influence in a case of no coating.

Then, for example, another hole is formed at a position adjacent to the position where the hole has been formed with the distal end of the marker 82 to which the ultrasonic vibration has been transmitted. Holes are formed in the biological tissue at appropriate intervals with the distal end of the marker 82 by repeating such an operation, thereby defining, e.g., a linear region (a cutting line) CL (see FIG. 5) as a treatment target or an annular region inside of which is a treatment target. That is, the treatment target region itself is marked or the outside of the treatment target region is marked. A description will be mainly given as to a case where the biological tissue is treated along the linear region CL hereinafter.

The rotary operation knob 92 is operated as required to rotate the probe unit 26 in a periaxial direction of the longitudinal axis L so that the treatment target region and the edge face region 74d of the treatment section 74 placed at a position close to the treatment target region can be observed with the arthroscope.

The edge face region 74d of the treatment section 74 in the probe unit 26 is moved to abut on the surface F of the biological tissue at a position close to the linear region CL.

In this state, when the switch section 16 is kept pressed, the ultrasonic transducer 52 is driven, and the ultrasonic vibration is oscillated, i.e., driven from the ultrasonic transducer unit 24. At this time, the edge face region 74d of the treatment section 74 enters from the surface F of the biological tissue in a depth direction (a direction to cut the biological tissue) by the effect of the ultrasonic vibration. A user appropriately moves the grip section 22 and cuts, namely, treats the biological tissue with the use of the edge face region 74 of the treatment section 74 along the linear region CL defined by forming holes.

At this time, the user performs cutting while confirming a cut state of the biological tissue with the arthroscope. Additionally, when a state that the linear region was cut by the ultrasonic vibration has been confirmed, the pressure on the switch section 16 is released. Therefore, driving of the ultrasonic transducer 52 is stopped.

It is to be noted that, when the marking has been annularly performed with the distal end of the marker 82, a treatment is given by, e.g., appropriately cutting an area within the circle with the edge face region 74d.

It is to be noted that a marking button and a treatment button may be provided in the switch section 16, respectively so that electric power to be output can be changed according to where the marking button is pressed and where the treatment button is pressed. For example, the electric power output from the power supply unit when the marking button is pressed may be set to be smaller than the electric power output from the power supply unit when the treatment button is pressed.

As described above, according to the treatment system 10 of this embodiment, the following can be said.

An operation of marking a treatment target position and an operation of giving a treatment to a marked treatment target can be performed to the biological tissue by using one probe unit 26. Thus, it is possible to eliminate an operation of changing over a treatment device for marking and a treatment device for a treatment, e.g., cutting from a non-illustrated port or the like. Thus, a treatment time in the case of treating the biological tissue can be shortened.

Further, even if there are two ports, i.e., a port in which the treatment device for marking can be arranged and a port in which the treatment device for a treatment, e.g., cutting can be arranged, since the single probe unit 26 according to this embodiment can perform the marking and the treatment, the number of the ports can be reduced, and the treatment devices can be prevented from interfering with each other. That is, the number of the treatment devices that can access the biological tissue at the same timing can be reduced, and the biological tissue can be treated while further decreasing the number of the treatment devices. Therefore, the probe unit 26 can treat the biological tissue in a less invasive manner.

Furthermore, the line-up of the treatment devices for marking that must be prepared in hospitals can be reduced.

Therefore, according to this embodiment, it is possible to provide the probe unit 26, the treatment device 12, and the treatment system 10 that can mark a region as a treatment target and treat the marked treatment target without requiring a changeover operation.

A hole can be formed in the biological tissue with the marker 82 protruding on the planar distal end face 74a of the treatment section 74 while transmitting the ultrasonic vibration to the probe unit 26 (the probe 62). At this time, even if the distal end face 74a abuts on the surface F of the biological tissue, the surface F of the biological tissue on which the distal end face 74a abuts can be prevented from being affected by the ultrasonic vibration.

A first modification of the first embodiment will now be described with reference to FIG. 6A to FIG. 6C. Here, like reference numerals denote the same members or members having the same functions as the members described in the first embodiment as much as possible to omit a description thereof here.

Figure 6A:
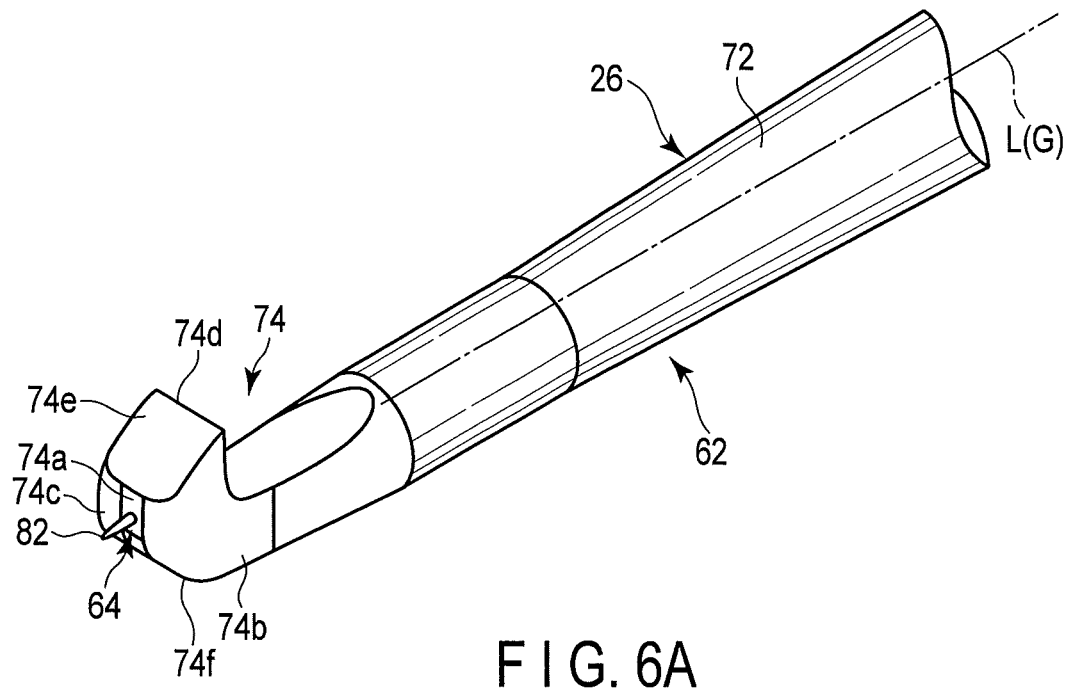
FIG. 6A is a schematic perspective view showing a hook-shaped treatment section and a knife-shaped marking section having a different width and a different thickness in a probe unit of a treatment device of a treatment system according to a first modification of the first embodiment.
Figure 6B:
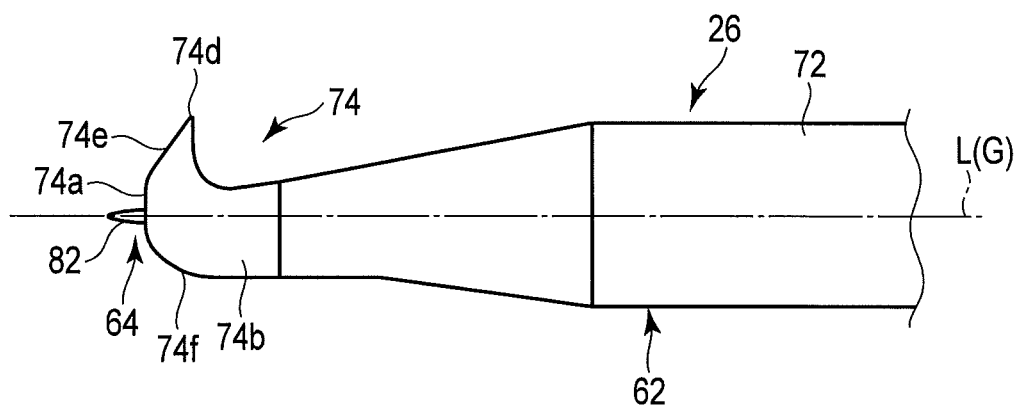
FIG. 6B is a schematic side elevation showing the hook-shaped treatment section and the knife-shaped marking section with a recognizable thickness in the probe unit of the treatment device of the treatment system according to the first modification of the first embodiment.

As shown in FIG. 6A to FIG. 6C, a distal end face 74a of a treatment section 74 according to this modification is formed to be continuous with curved side surfaces 74b and 74c. Each of a boundary between the distal end face 74a and the side surface 74b and a boundary between the distal end face 74a and the side surface 74c is formed as an obtuse angle that is larger than 90° and smaller than 180°, namely, close to 180°. Therefore, the distal end face 74a is smoothly continuous with the side surface 74b, and the distal end face 74a is smoothly continuous with the side surface 74c, respectively. Even if the distal end face 74a is formed in this manner, it functions as a regulation surface that regulates entrance of a marker 82 into a biological tissue when the distal end face 74a of the treatment section 74 is moved to abut on a surface F of the biological tissue.

The marker 82 according to this modification is formed into a knife-like shape having a thickness shown in FIG. 6B smaller than a width shown in FIG. 6C. It is preferable to form the marker 82 to be symmetrical to a longitudinal axis L. As shown in FIG. 7A, this marker 82 can form holes by using ultrasonic vibration like the description of the first embodiment. Each hole in this example is formed in accordance with a shape of a distal end (a function region of the ultrasonic vibration) of the knife-shaped marker 82. Moreover, a linear region (a cutting line) CL of a treatment target, an annular region inside of which is a treatment target, or the like is defined by appropriately forming holes at appropriate intervals with the use of the knife-shaped marker 82.

The marker 82 according to this modification can mark a relatively soft biological tissue such as a cartilage like drawing a line by using the ultrasonic vibration as shown in FIG. 7B. Specifically, holes are formed in a surface of the biological tissue by pressing a switch section 16 shown in FIG. 1 to oscillate the ultrasonic vibration. The pressure on the switch 16 is kept to move the marker 82 in a direction orthogonal to an axial direction. Thus, the surface F of the biological tissue is linearly marked by the marker 82.

A second modification of the first embodiment will now be described with reference to FIG. 8A and FIG. 8B. Here, like reference numerals denote the same members or members having the same functions as the members described in the first embodiment as much as possible to omit a description thereof here.

Figure 8A:
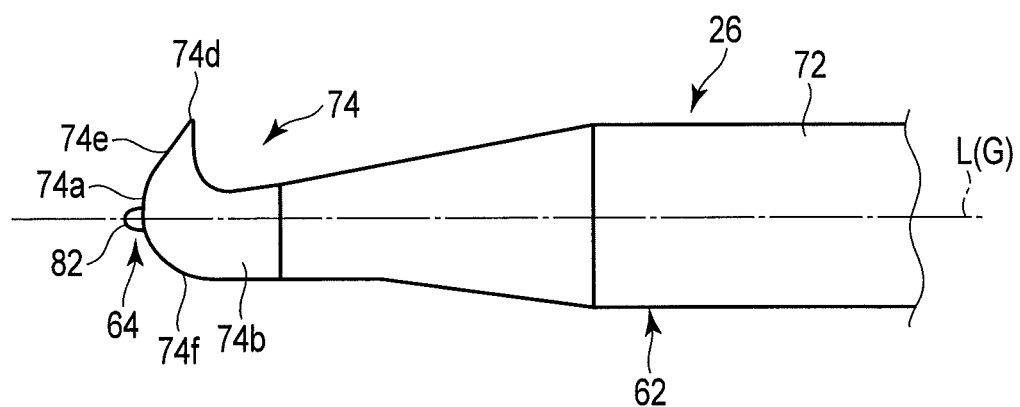
FIG. 8A is a schematic side elevation showing a hook-shaped treatment section and a marking section in a probe unit of a treatment device of a treatment system according to a second modification of the first embodiment.
Figure 8B:
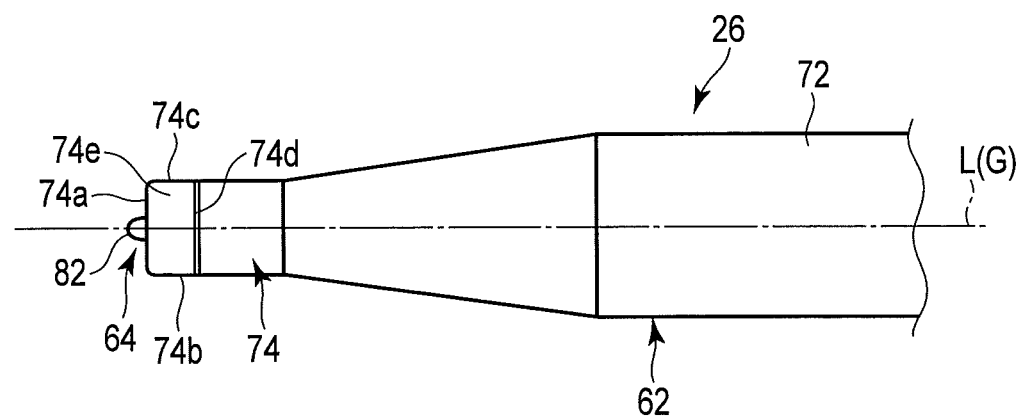
FIG. 8B is a schematic top view showing the hook-shaped treatment section and the marking section in the probe unit of the treatment device of the treatment system according to the second modification of the first embodiment.

As shown in FIG. 8A and FIG. 8B, a distal end face 74a of a treatment section 74 according to this modification is formed as a curved surface portion that is smoothly continuous with continuous surfaces 74e and 74f. The distal end face 74a and regions of the continuous surfaces 74e and 74f close to the distal end face 74a are preferably subjected to low-friction coating. The distal end face 74a functions as a regulation surface that regulates entrance of a marker 82 into a biological tissue. That is, the distal end face 74a of the treatment section 74 functions as a stopper that defines an amount of entrance of the marker 82 (a marking section 64) into the biological tissue.

Thus, it can be easily understood that the distal end face 74a of the treatment section 74 may be formed as a flat surface portion or may be formed as a curved surface portion.

A third modification of the first embodiment will now be described hereinafter with reference to FIG. 9A and FIG. 9B. Here, like reference numerals denote to the same members or members having the same functions as the members described in the first embodiment as much as possible to omit a description thereof here.

As shown in FIG. 9A and FIG. 9B, in a marking section 64 according to this modification, a marker 82 is eliminated from a distal end face 74a of a treatment section 74, and a pair of markers 84 and 86 are arranged on side surfaces 74b and 74c of the treatment section 74 instead. In this modification, it is preferable to form pairs, e.g., one pair of the marking sections 64. The markers 84 and 86 are provided at positions deviating from a longitudinal axis L and formed at positions where a vibration balance of ultrasonic vibration transmitted to the treatment section 74 is prevented from being broken, i.e., positions where abnormal vibration is avoided. The markers 84 and 86 are formed at positions orthogonal to a virtual center of gravity line G (near central portions of the side surfaces 74b and 74c).

It is to be noted that the side surfaces 74b and 74c are preferably subjected to low-friction coating that more greatly reduces a friction force on a biological tissue than on other regions.

Each of the markers 84 and 86 of the marking section 64 is formed into a size smaller than the treatment section 74 of a probe 62. Each of the markers 84 and 86 is preferably formed into, e.g., a semispherical shape or a substantially elliptic conical shape.

A function of a treatment system 10 according to this embodiment will now be briefly described.

A hole is formed in a biological tissue or the biological tissue is slightly cut by using one of the pair of markers 84 and 86 to which the ultrasonic vibration has been transmitted. In this manner, the treatment target region itself is marked, or the outside of the treatment target region is marked.

It is to be noted that, when the side surface 74b of the treatment section 74 is allowed to abut on the surface F of the biological tissue, the side surface 74b functions as a regulation surface that regulates entrance of the marker 84 into the biological tissue. That is, the side surface 74b of the treatment section 74 functions as a stopper that defines an amount of entrance of the marker 84 (the marking section 64) into the biological tissue. The amount of entrance of the marker 84 into the surface F of the biological tissue is defined by a length of the marker 84 along the longitudinal axis L. The side surface 74b of the treatment section 74 is formed to have a larger surface area than the distal end (the function region of the ultrasonic vibration) of the marker 84 (the marking section 64). Thus, when the ultrasonic vibration is transmitted to the treatment section 74, the biological tissue abutting on the distal end face 74a can be prevented from being affected by the ultrasonic vibration, and the biological tissue can be protected. In particular, since the side surface 74b has been subjected to low-friction coating, an influence of transmission of the ultrasonic vibration on the biological tissue that can abut on the side surface 74b due to the ultrasonic vibration can be reduced to be smaller than an influence in a case of no coating. This can be likewise applied to a relationship between the side surface 74c and the marker 86.

Further, a treatment such as cutting with an edge face region 74d is given to the marked region itself, or a treatment such as cutting with the edge face region 74d is given to the treatment target region inside the marked position.

According to this modification, it is possible to provide the probe unit 26, the treatment device 12, and the treatment system 10 that can mark a region as a treatment target and treat the marked treatment target without requiring a changeover operation.

A fourth modification of the first embodiment will now be described hereinafter with reference to FIG. 10A.

The treatment section 74 in each of the first embodiment and the first modification to the third modification of the first embodiment has been described as the hook type. As shown in FIG. 10A, a treatment section 74 of a probe 62 may be configured as a rake type formed into a rake shape. An edge face region 74d of the rake-shaped treatment section 74 is formed in an appropriate range in a direction orthogonal to a longitudinal axis L.

Here, a marking section 64 includes a first marker 82 arranged on a distal end face 74a of the treatment section 74, and second and third markers 84 and 86 arranged on side surfaces 74b and 74c of the treatment section 74. In this manner, it is also preferable to use an appropriate combination of the marking section 64 in the first embodiment and the marking section 64 in the third modification of the first embodiment (see FIG. 9A and FIG. 9B).

Therefore, in a state that ultrasonic vibration has been transmitted to the probe unit 26, a biological tissue can be marked to define a treatment target region by using at least one of the first to third markers 82, 84, and 86, and a treatment such as cutting using the edge face region 74d can be given with the use of the same probe unit 26 after the marking to the treatment target region defined by the marking.

Here, it is assumed that the distal end face 74a of the treatment section 74 is formed as a flat surface portion. Furthermore, the distal end face 74a is smoothly continuous with a continuous surface 74e, and the distal end face 74a is smoothly continuous with a continuous surface 74f, respectively. Moreover, the distal end face 74a of the treatment section 74 functions as a stopper that regulates an amount of entrance of the marker 82 (the marking section 64) into the biological tissue. Additionally, the side surfaces 74b and 74c are formed as curved surface portions, respectively.

A size (a surface area) of a distal end (a function region of the ultrasonic vibration) of the marker 82 of the marking section 64 in particular is formed to be sufficiently smaller than a surface area of the distal end face 74a of the treatment section 74 of the probe 62. Thus, when the ultrasonic vibration has been transmitted to the treatment section 74, the biological tissue abutting on the distal end face 74a can be prevented from being affected by the ultrasonic vibration, and the biological tissue can be protected.

Figure 10A:
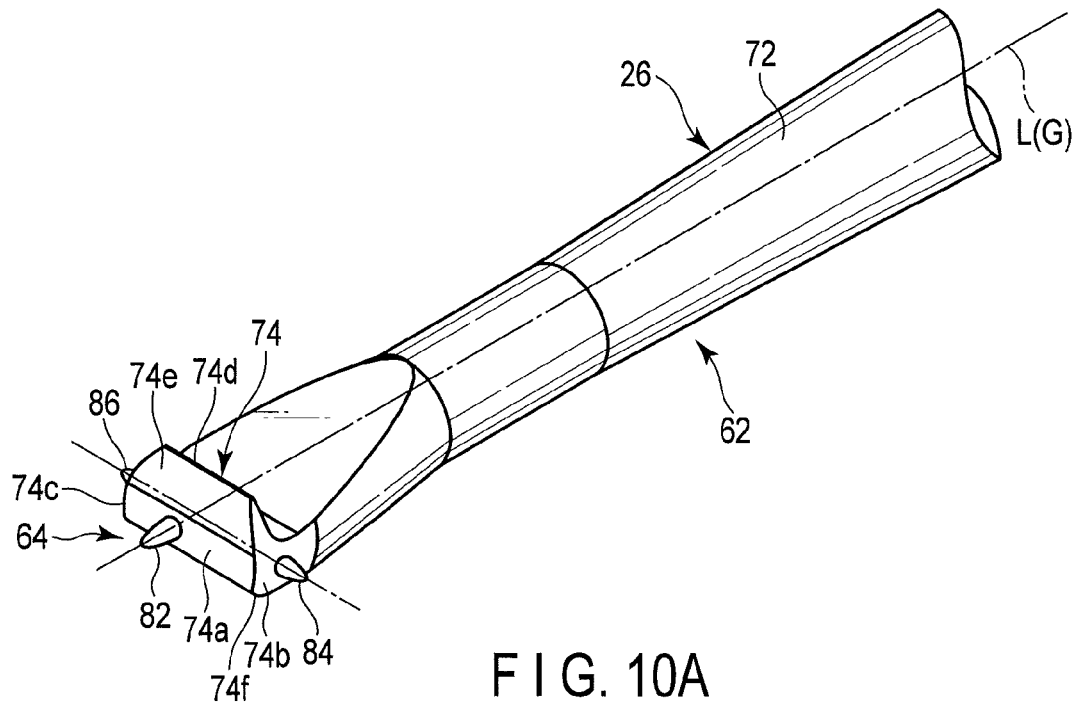
FIG. 10A is a schematic perspective view showing a rake-shaped treatment section and a marking section in a probe unit of a treatment device of a treatment system according to a fourth modification of the first embodiment.
Figure 10B:
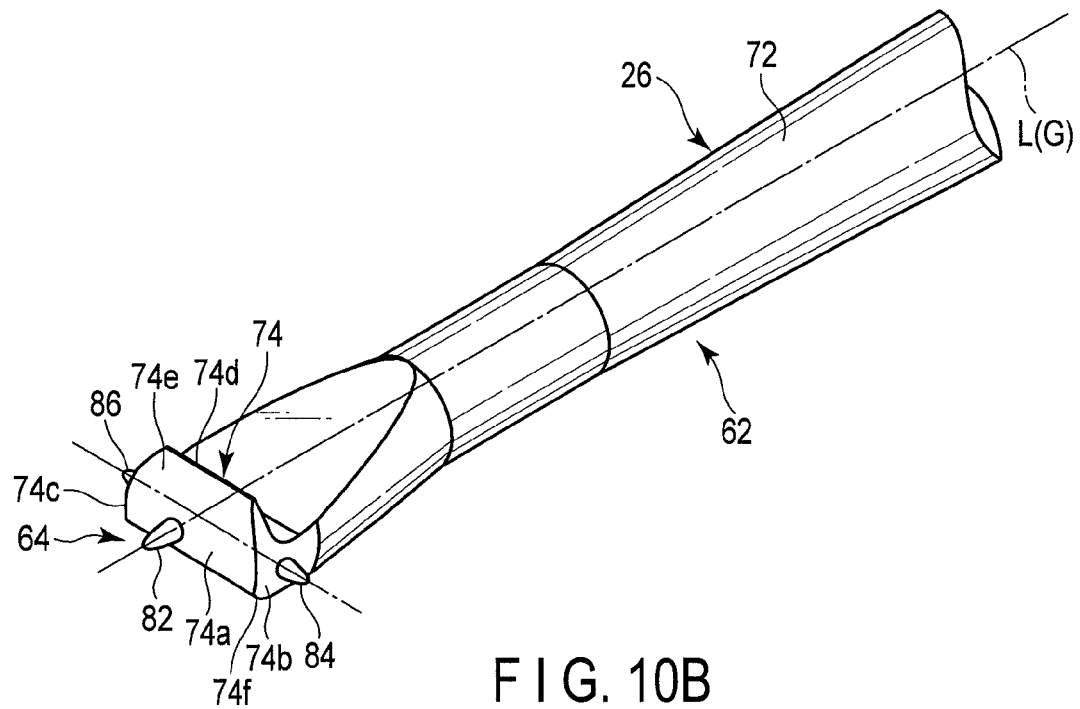
FIG. 10B is a schematic perspective view showing a rake-shaped treatment section and a marking section in a probe unit of a treatment device of a treatment system according to a further modification of the fourth modification of the first embodiment.

Even if the distal end face 74a of the treatment section 74 is formed as the curved surface portion like the probe 62 shown in FIG. 10B, it is possible to use it like the probe 62 shown in FIG. 10A.

Thus, it can be easily understood from the first embodiment and the fourth modification of the first embodiment that the side surfaces 74b and 74c on which the markers 84 and 86 are arranged respectively in the treatment section 74 may be formed as the flat surface portions or may be formed as the curved surface portions.

A fifth modification of the first embodiment will now be described with reference to FIG. 11A.

Figure 11A:
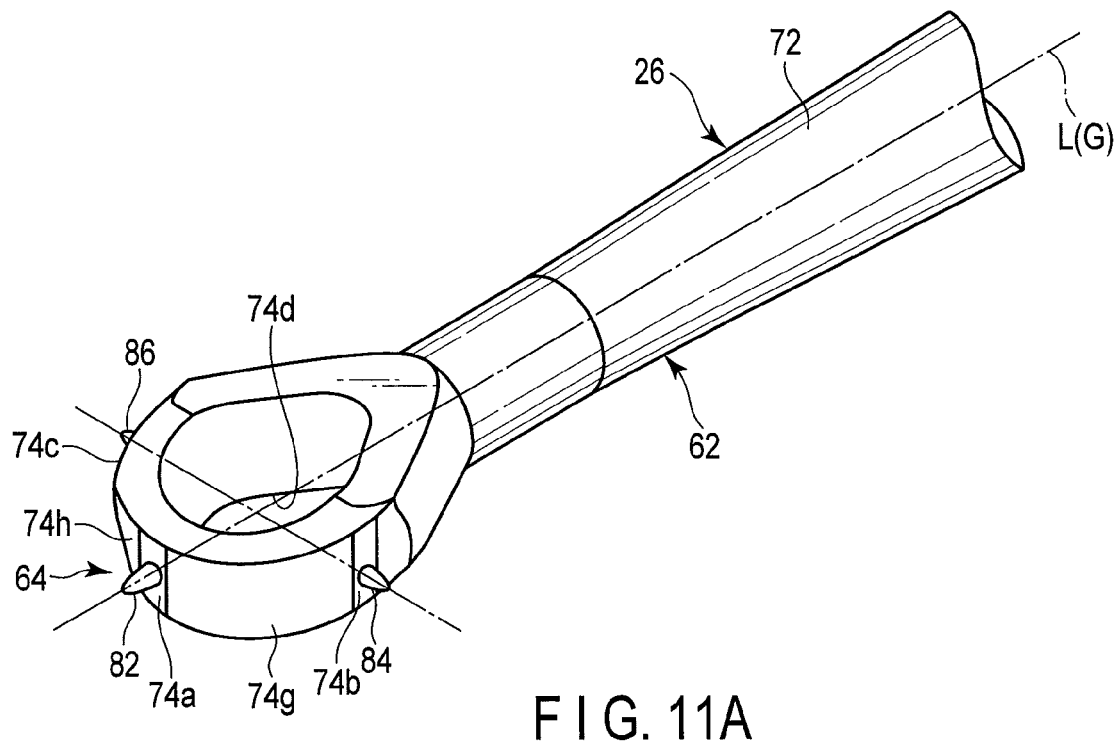
FIG. 11A is a schematic perspective view showing a curette-shaped treatment section and a marking section in a probe unit of a treatment device of a treatment system according to a fifth modification of the first embodiment.

As shown in FIG. 11A, a treatment section 74 of a probe 62 may be formed as a curette type.

As shown in FIG. 11A, a distal end face 74a of the treatment section 74 is formed as a flat surface portion on which a marker 82 is arranged. Side surfaces 74b and 74c of the treatment section 74 are formed as flat surface portions on which markers 84 and 86 are arranged, respectively. Additionally, curved surfaces 74g and 74h are formed between the distal end face 74a and the side surfaces 74b and 74c, respectively. A boundary between the distal end face 74a and the curved surface 74g, a boundary between the curved sur face 74g and the side surface 74b, a boundary between the distal end face 74a and the curved surface 74h, and a boundary between the curved surface 74h and the side surface 74c are smoothly continuous, respectively.

The distal end face 74a functions as a regulation surface that regulates entrance of the marker 82 into a biological tissue. That is, the distal end face 74a of the treatment section 74 functions as a stopper that defines an amount of entrance of the marker 82 (a marking section) 64 into the biological tissue. Likewise, the side surfaces 74b and 74c function as regulation surfaces that regulate entrance of the markers 84 and 86 into the biological tissue. That is, the side surfaces 74b and 74c of the treatment section 74 function as stoppers that define amounts of entrance of the markers 84 and 86 (the marking section 64) into the biological tissue.

The distal end face 74a of the treatment section 74 is formed to have a larger surface area than a distal end (a function region of the ultrasonic vibration) of the marker 82 (the marking section 64). Thus, when the ultrasonic vibration has been transmitted to the treatment section 74, the biological tissue abutting on the distal end face 74a can be prevented from being affected by the ultrasonic vibration, and the biological tissue can be protected. Likewise, the side surfaces 74b and 74c are formed to have surface areas larger than distal ends (function regions of the ultrasonic vibration) as tips of the markers 84 and 86, respectively. Thus, when the ultrasonic vibration has been transmitted to the treatment section 74, the biological tissue abutting on the side surfaces 74b and 74c can be prevented from being affected by the ultrasonic vibration, and the biological tissue can be protected.

An edge face region 74d of the curette-shaped treatment section 74 is formed in an appropriate range in a direction orthogonal to a longitudinal axis L. The edge face region 74d of the curette-shaped treatment section 74 is annularly formed. When the edge face region 74d is allowed to abut on a surface F of the biological tissue, marking and a treatment can be performed like the treatment devices 12 described in each of the first embodiment and the third and fourth modifications of the first embodiment.

Figure 11B:
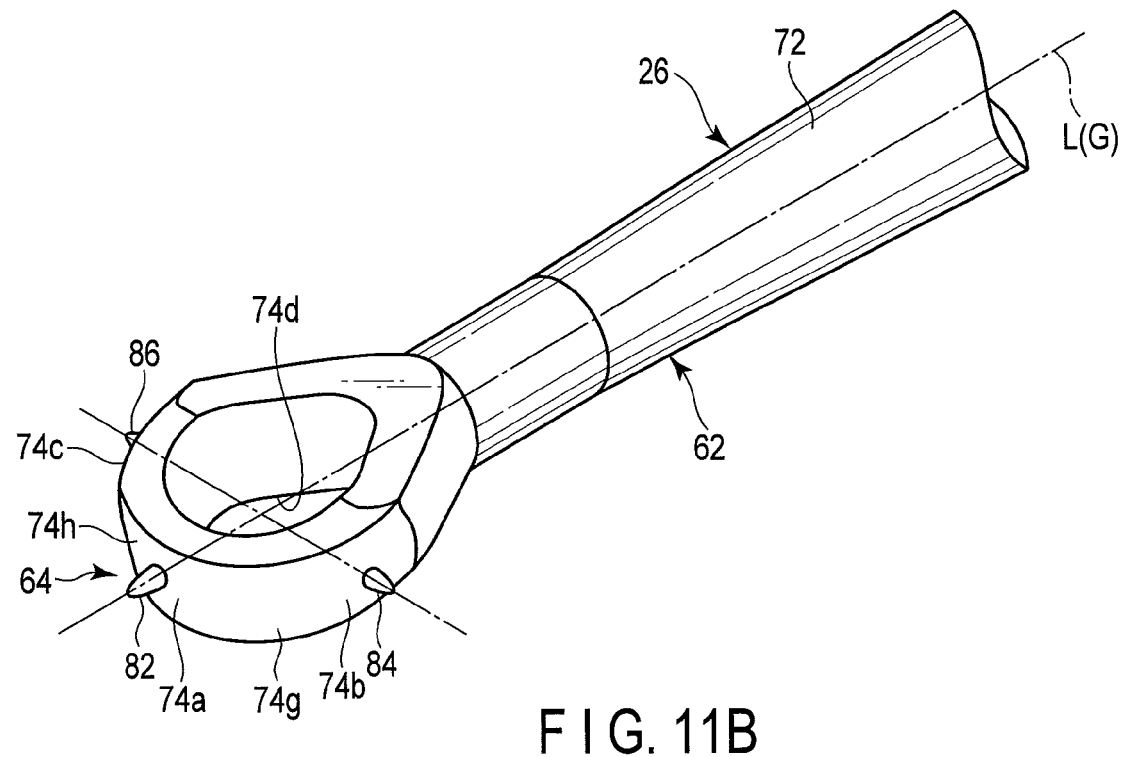
FIG. 11B is a schematic perspective view showing a curette-shaped treatment section and a marking section in a probe unit of a treatment device of a treatment system according to a further modification of the fifth modification of the first embodiment.

Even if the distal end face 74a and the side surfaces 74b and 74c of the treatment section 74 are formed as curved surface portions respectively like the probe 62 shown in FIG. 11B, it is possible to use them like the probe 62 shown in FIG. 11A.

It is to be noted that using the treatment sections 74 shown in FIG. 10A to FIG. 11B for a treatment, e.g., cutting an articular cartilage is preferable like the hook-shaped treatment section 74 described in the first embodiment.

Further, various shapes can be adopted for the treatment section 74.

A second embodiment will now be described with reference to FIG. 12 to FIG. 13B. This embodiment is a modification of the first embodiment including the respective embodiments, and like reference numerals denote the same members or members having the same functions as the members described in the first embodiment as much as possible to omit a description thereof.

A probe unit 126 of a treatment device 112 according to this embodiment includes a probe 162 and a marking section 164 that is arranged in a later-described pipeline 120 of the probe 162. A power supply unit 114 includes a high-frequency power supply 14a that supplies high-frequency energy to a later-described electrode 182 of the marking section 164 and an ultrasonic vibration power supply 14b that supplies electric power to an ultrasonic transducer unit 24.

The probe 162 includes a probe main body (a vibration transmitting section) 172 and a treatment section 174. Here, a description will be given on the assumption that there is adopted the treatment section 174 formed like the hook-shaped treatment section 174 explained in the first embodiment except for presence of the later-described pipeline 120. Further, the marker 82 described in the first embodiment is not provided on a distal end face 74a of the treatment section 174.

The pipeline 120 is formed in the probe 162 and the ultrasonic transducer unit 24 along a longitudinal line L. A proximal end of the pipeline 120 is extended to a proximal end side of a proximal end of the ultrasonic transducer unit 24 and supported by a pipeline protector 120a arranged at a proximal end of an exterior case 42 of a grip section 22. It is to be noted that the pipeline protector 120a is aligned with a cable 18.

The pipeline 120 is formed of itself in the probe 162 and the ultrasonic transducer unit 24, and it is formed of a tube 122 on the proximal end side of the ultrasonic transducer unit 24.

Here, a distal end of the pipeline 120 is present on the distal end face 74a of the treatment section 174 in the probe 162 as shown in FIG. 13A and FIG. 13B. A proximal end of the pipeline 120 is a proximal end of the tube 122 as shown in FIG. 12.

Figure 12:
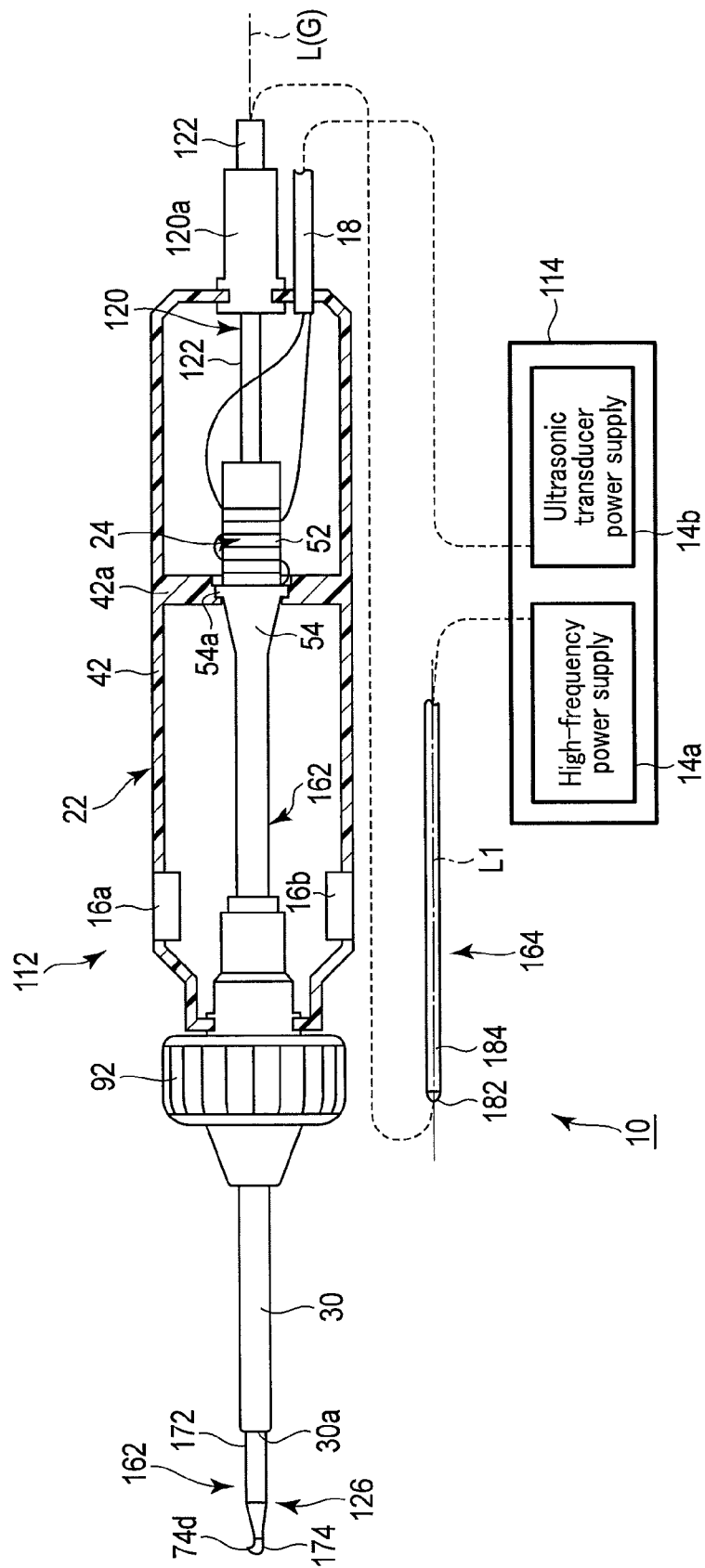
FIG. 12 is a schematic partial longitudinal sectional view showing a treatment system according to a second embodiment.

As shown in FIG. 12, the marking section 164 is formed as a linear member that can be inserted into or removed from the pipeline 120. Although it is preferable to make the marking section 164 using a flexible material having flexibility, it is also preferable to make it using a material having rigidity that maintains a straight state.

Here, the linear axis L is defined to the probe 162 by the probe main body (the vibration transmitting section) 172 and the treatment section 174, and a longitudinal axis L1 of the marking section 164 is arranged parallel to the longitudinal axis L of the probe 162.

A proximal end of the marking section 164 is electrically connected to the high-frequency power supply 14a of the power supply unit 114. A distal end of the marking section 164 is used as a first high-frequency electrode 182 that marks a biological tissue. A proximal end side of the region used as the first high-frequency electrode 182 is covered with a material having electrical insulating properties. That is, an outer peripheral surface of the marking section 164 is covered with a covering material 184 having electrical insulating properties except for the distal end (the first high-frequency electrode 182). It is preferable for a material of this covering material 184 to have heat resistance and abrasion resistance since ultrasonic vibration may be transmitted thereto in a state that the marking section 164 is inserted in the pipeline 120. As a material of the covering material 184, for example, PTFE is used.

The marking section 164 can be inserted into or removed from the pipeline 120 from the proximal end thereof. At this time, as shown in FIG. 13A and FIG. 13B, the distal end of the marking section 164, i.e., the first high-frequency electrode 182 can be protruded on the distal end face 74a of the treatment section 174, i.e., the distal end of the pipeline 120 toward the distal end side along the longitudinal axis L. Further, the distal end of the marking section 164 can be moved to the proximal end side from the distal end of the pipeline 120 along the longitudinal axis L to retract the distal end of the marking section 164 toward the proximal end side from the distal end of the pipeline 120 (the distal end face 74a of the treatment section 174).

That is, the probe 162 includes the pipeline 120 that pierces through the probe main body 172 and the treatment section 174 along the longitudinal axis L and can move in the marking section 164 along the longitudinal axis L, and the distal end of the marking section 164 can protrude from and retract into the distal end of the pipeline 120.

The probe 162 according to this embodiment not only transmits the ultrasonic vibration, but functions as a second high-frequency electrode. Therefore, the probe 162 can flow a high-frequency current through a biological tissue between the first high-frequency electrode 182 of the marking section 164 and itself.

It is to be noted that a hand switch according to this embodiment includes a first switch section 16a and a second switch section 16b. The first switch section 16a is set to apply high-frequency energy between the first high-frequency electrode 182 of the marking section 164 and the probe 162 as the second high-frequency electrode when it is pressed. The second switch section 16b is set to drive the ultrasonic transducer 52 so that the ultrasonic vibration can be transmitted to the treatment section 174 of the probe 162 when it is pressed.

A function of a treatment system 10 according to this embodiment will now be briefly described.

The marking section 164 is arranged from the proximal end (the proximal end of the tube 122) to the distal end (the distal end face 74a of the treatment section 174) of the pipeline 120 in advance. At this time, it is preferable to arrange the marking section 164 so that the first high-frequency electrode 182 at the distal end of the marking section 164 does not protrude from the distal end of the pipe 120.

The treatment section 174 is moved to access a biological tissue as a treatment target from a non-illustrated port or the like while observing the biological tissue as the treatment target with an arthroscope or the like.

In this state, the marking section 164 is moved to be pushed into a grip section 22 so that the distal end of the marking section 164 protrudes on the distal end of the treatment section 174 as shown in FIG. 13A and FIG. 13B. In a state that the first high-frequency electrode 182 at the distal end of the marking section 164 abuts on the biological tissue, the first switch section 16a is operated to cauterize the biological tissue (e.g., a periosteum (a surface of a cortical bone)) between the first high-frequency electrode 182 at the distal end of the marking section 164 and the probe 162, i.e., the second high-frequency electrode until the biological tissue discolors. Here, since the biological tissue is cauterized to clarify a treatment line (a cutting line) or clarify a treatment range, it is preferable to perform cauterization until the biological tissue discolors. Therefore, if the cauterization has been performed with the distal end of the first high-frequency electrode 182 until the biological tissue discolors, the pressure on the first switch section 16a is released, and application of high-frequency energy is stopped.

In a state that the distal end of the marking section 164 abuts on a position adjacent to the cauterized position, the first switch section 16a is operated, and the position abutting on the distal end of the marking section 164 is cauterized until it discolors.

Such an operation is repeated to define, e.g., a linear region (a cutting line) CL (see FIG. 5) as a treatment target or an annular region inside of which is a treatment target of the biological tissue. That is, the treatment target region itself is marked, or the outside of the treatment target region is marked.

Then, the second switch section 16b is pressed to give a treatment, e.g., cutting to the linear region CL as the treatment target or the inside of the annular region as the treatment target while maintaining a state that the treatment section 174 has accessed the biological tissue as the treatment target.

Thus, the treatment device 112 according to this embodiment can be used in substantially the same manner as the treatment device 12 described in the first embodiment.

Thus, according to this embodiment, it is possible to provide the probe unit 126, the treatment device 112, and the treatment system 10 that can mark a region as a treatment target and treat the marked treatment target without requiring a changeover operation.

It is to be noted that, in this embodiment, the description has been given as to the example adopting a bipolar type in which the probe 162 is used as the second high-frequency electrode but, as a matter of course, it is also possible to adopt a monopolar type by attaching a counter electrode plate (not shown) to a patient without using the probe 162 as the second high-frequency electrode.

Furthermore, it is also obviously preferable that the pair of markers 84 and 86 described in the first modification of the first embodiment can be formed on the side surfaces 74b and 74c of the treatment section 174 according to this embodiment. In this case, the first high-frequency electrode 182 at the distal end of the marking section 164 can be employed for marking using the high-frequency energy, and the pair of markers 84 and 86 can be employed for marking using the ultrasonic vibration.

Moreover, even if the treatment sections 74 formed into the shapes shown in FIG. 10A to FIG. 11B are provided, forming a pipeline 120 like the pipeline 120 described in this embodiment enables using the probe 162 as well as the marking section 164.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A probe which is configured to treat a bone by ultrasonic vibration, comprising:
    a vibration transmitting section that defines a longitudinal axis along which the ultrasonic vibration is transmitted from a proximal end side toward a distal end side; and
    a treatment section which is arranged on the distal end side of the vibration transmitting section, to which the ultrasonic vibration is transmitted through the vibration transmitting section, the treatment section including:
        a cutting blade that includes a treatment surface which protrudes in a direction crossing the longitudinal axis, and cuts and treats the bone by the treatment surface;
        a protrusion that is provided at a position different from the cutting blade, protrudes in a direction different from the protruding direction of the treatment surface of the cutting blade, marks the bone, and defines a position of the bone to be treated with the cutting blade; and
        a regulation surface that is formed at a position where the protrusion is provided, and regulates entrance of the protrusion into the bone beyond a predetermined level.

2. The probe according to claim 1, wherein a contact area of the treatment surface of the cutting blade that comes into contact with the bone is larger than a contact area of the protrusion that comes into contact with the bone.

3. The probe according to claim 1, wherein the regulation surface is formed of a flat surface or a curved surface, and the protrusion protrudes from the flat surface or the curved surface.

4. The probe according to claim 1, wherein the protrusion protrudes in a direction of the longitudinal axis.

5. A treatment device comprising:
    a probe according to claim 1; and
    a transducer unit that is connected with the probe and generates ultrasonic vibration.

6. A treatment system comprising:
    a treatment device according to claim 5; and
    a power supply unit that supplies electric power to the treatment device.

* * * * *